US008623597B2

(12) United States Patent
Mamine et al.

(10) Patent No.: US 8,623,597 B2
(45) Date of Patent: *Jan. 7, 2014

(54) BIOASSAY METHOD, BIOASSAY DEVICE, AND BIOASSAY SUBSTRATE

(75) Inventors: Takayoshi Mamine, Kanagawa (JP); Takuro Yamamoto, Osaka (JP)

(73) Assignee: Sony Corporation, Tokyo (JP)

( * ) Notice: Subject to any disclaimer, the term of this patent is extended or adjusted under 35 U.S.C. 154(b) by 556 days.

This patent is subject to a terminal disclaimer.

(21) Appl. No.: 10/484,134

(22) PCT Filed: May 21, 2003

(86) PCT No.: PCT/JP03/06341
§ 371 (c)(1),
(2), (4) Date: Jan. 16, 2004

(87) PCT Pub. No.: WO03/098216
PCT Pub. Date: Nov. 27, 2003

(65) Prior Publication Data
US 2005/0069880 A1     Mar. 31, 2005

(30) Foreign Application Priority Data

May 21, 2002 (JP) ................................ 2002-146904
May 22, 2002 (JP) ................................ 2002-147301

(51) Int. Cl.
*C12Q 1/68* (2006.01)
*C12M 1/00* (2006.01)
*C12M 1/34* (2006.01)
*C12M 3/00* (2006.01)

(52) U.S. Cl.
USPC .... 435/6.1; 435/283.1; 435/287.1; 435/287.2

(58) Field of Classification Search
USPC .............................. 435/6, 283.1, 287.1, 287.2
See application file for complete search history.

(56) References Cited

U.S. PATENT DOCUMENTS

| 5,445,934 A | | 8/1995 | Fodor et al. | |
|---|---|---|---|---|
| 5,605,662 A | * | 2/1997 | Heller et al. | .................. 422/68.1 |
| 5,632,957 A | * | 5/1997 | Heller et al. | .................. 422/68.1 |
| 5,788,819 A | * | 8/1998 | Onishi et al. | .................. 205/155 |

(Continued)

FOREIGN PATENT DOCUMENTS

| EP | 1 132 484 A2 | 3/2001 |
|---|---|---|
| EP | 1 211 325 A2 | 6/2002 |

(Continued)

OTHER PUBLICATIONS

Stanley, Norman F., "Agars," in "Food Polysaccharides and Their Applications," Stephen, Alistair M., ed., Marcel Dekker, Inc., New York, 1995.*

(Continued)

*Primary Examiner* — Robert T. Crow
(74) *Attorney, Agent, or Firm* — Finnegan, Henderson, Farabow, Garrett & Dunner, LLP

(57) ABSTRACT

Disclosed is a bioassay method in which, by controlling the electric field formation in the reaction region where an interaction between substances, such as a hybridization, is performed, the efficiency of the interaction can be improved. Also disclosed is a bioassay apparatus in which the method can be favorably carried out. The method includes at least a step of turning on/off the electric field formation by the electric field-forming means E at a predetermined timing.

14 Claims, 6 Drawing Sheets

(56) References Cited

U.S. PATENT DOCUMENTS

| | | | |
|---|---|---|---|
| 5,807,522 A | 9/1998 | Brown et al. | |
| 5,849,486 A | 12/1998 | Heller et al. | |
| 5,922,617 A * | 7/1999 | Wang et al. | 436/518 |
| 6,022,748 A * | 2/2000 | Charych et al. | 436/527 |
| 6,051,380 A * | 4/2000 | Sosnowski et al. | 435/6 |
| 6,099,803 A * | 8/2000 | Ackley et al. | 422/68.1 |
| 6,183,970 B1 | 2/2001 | Okano et al. | |
| 6,290,839 B1 | 9/2001 | Kayyem et al. | |
| 6,338,820 B1 * | 1/2002 | Hubbard et al. | 422/64 |
| 2002/0029969 A1 * | 3/2002 | Yager et al. | 204/455 |
| 2002/0043463 A1 * | 4/2002 | Shenderov | 204/450 |
| 2002/0055103 A1 | 5/2002 | Barton et al. | |
| 2002/0086416 A1 * | 7/2002 | Sato et al. | 435/287.2 |
| 2002/0137066 A1 * | 9/2002 | Kajiyama et al. | 435/6 |

FOREIGN PATENT DOCUMENTS

| | | |
|---|---|---|
| EP | 1 231 214 | 8/2002 |
| JP | 11-512605 | 11/1999 |
| JP | 2000-60554 | 2/2000 |
| JP | 2000-060554 | 2/2000 |
| JP | 2000-279169 | 10/2000 |
| JP | 2001-238674 | 9/2001 |
| JP | 2001-321198 | 11/2001 |
| JP | 2002-168864 | 6/2002 |
| JP | 2002-228684 | 8/2002 |
| JP | 2003-514227 | 4/2003 |
| WO | WO 97/12030 | 4/1997 |
| WO | WO 98/28320 | 7/1998 |

OTHER PUBLICATIONS

Masao Washizu et al, "Applications of Electrostatic Stretch-and-Positioning of DNA", IEEE Transactions on Industry Applications, Inc., May 1, 1995, vol. 31, No. 3, pp. 447-456.

Seiichi Suzuki et al.; "Quantitative Analysis on Electrostatic Orientation of DNA in Stationary AC Electric Field Using Fluorescence Anisotropy"; IEEE Transaction on Industrial Applications; vol. 34, No. 1; pp. 75-83; (1998).

Masao Washizu, et al., "Electric Manipulation of DNA in Micro fabricated Structures", IEEE Transactions on Industry Applications, vol. 26, No. 6, pp. 1165-1172.

US 6,200,755, 03/2001, Virtanen (withdrawn)

* cited by examiner

BIOASSAY METHOD, BIOASSAY DEVICE, AND BIOASSAY SUBSTRATE

TECHNICAL FIELD

The present invention relates to bioassay methods, bioassay apparatuses, and bioassay substrates which are particularly useful in the bioinformatics (life information science) field.

BACKGROUND ART

The main conventional techniques which are related to the present invention will be described below.

Currently, integrated substrates for bioassays, i.e., so-called DNA chips or DNA microarrays, (hereinafter referred to as "DNA chips"), in which selected DNA is microarrayed by microarray technology, have been used for the analysis of gene mutations, SNP (single nucleotide polymorphism) analysis, gene expression frequency analysis, etc., and have also started to be used extensively for the development of new drugs, clinical diagnosis, pharmacogenomics, forensic medicine, and other fields.

The DNA chips are characterized in that it is possible to extensively analyze intermolecular interactions, such as hybridizations, because various types and a large number of DNA oligomer chains, cDNA (complementary DNA), etc., can be integrated on glass substrates or silicon substrates.

One example of analytical methods using DNA chips will be briefly described below. That is, PCR amplification is performed in which mRNA extracted from cells, tissues, etc., is incorporated by reverse transcription-PCR or the like into DNA probes solid-phased on a glass substrate or silicon substrate, and hybridization is performed on the substrate. Fluorescent light measurement is then carried out with a suitable detector.

DNA chips can be classified into two types. In the first type of chip, oligonucleotides are synthesized directly on a given substrate using photolithography by applying semiconductor exposure technology. A typical example is the one manufactured by Affymetrix, Inc., U.S.A. (for example, refer to U.S. Pat. No. 5,445,934). In this type of chip, although the integration degree is high, DNA synthesis on the substrate has limitations, and the length is limited to about several tens of bases.

In the second type of chip, which is also referred to as "the Stanford method", the chip is fabricated by dispensing and solid-phasing prepared DNA on a substrate using a split taper pin (for example, refer to U.S. Pat. No. 5,807,522). In this type of chip, although the integration degree is lower than that of the former type, it is possible to solid-phase about 1 kb of DNA fragments.

Recently, biosensor technology has been advancing, in which a selected detecting substance is solid-phased on a fine detection surface site provided on a thin plate, which is referred to as a biosensor chip, such as a protein chip, and a microvolume of solution containing a target substance is allowed to flow toward the detecting substance, and then the interaction between the two substances is observed and analyzed based on the surface plasmon resonance principle, quartz crystal oscillator principle, or the like. This technology is becoming useful for analyzing interactions between substances, such as antibody-antigen reactions and hormone responses.

In the conventional DNA chip technology and biosensor technology, however, interactions between substances, such as hybridization reactions and antibody-antigen reactions, are carried out by solid-phasing (immobilizing) detecting nucleotide chains, such as DNA probes, and proteins, etc., on two-dimensional, small detection regions of substrates. Consequently, the interactions are carried out mainly based on the Brownian movement of the reaction products under not necessarily favorable reaction conditions in which freedom of the reaction products is limited spatially and there is also a possibility that steric hindrance may occur during the reactions. Therefore, the conventional DNA chip technology and biosensor technology have technical problems, i.e., low interaction efficiency and long reaction time.

Furthermore, in the known DNA chips, etc., sample solutions are only dripped onto predetermined spot sites (detection regions) on substrates, and no devices are used to relatively align the target substances contained in the sample solutions and the detecting substances immobilized on the spot sites.

Accordingly, it is a principal object of the present invention to provide a bioassay method, a bioassay apparatus, and a bioassay substrate that can be advantageously used in the bioassay method and the bioassay apparatus, in which, by controlling the electric field formation in the reaction region where an interaction between substances, such as a hybridization, is carried out, the detecting substance and the target substance are relatively aligned with each other, and the structures of the substances are adjusted, thereby increasing the efficiency of the interaction.

DISCLOSURE OF INVENTION

In order to overcome the technical problems described above, in one aspect of the present invention, the following "bioassay method" is provided. Additionally, in the present invention, the term "bioassay" widely means biochemical analysis based on interactions between substances, such as hybridizations.

In the "bioassay method" of the present invention, an interaction between substances is detected by a detecting element, the detecting element including at least a detection surface which is surface-treated for immobilizing a detecting substance, a reaction region which provides a field for interaction between the detecting substance immobilized on the detection surface and a target substance, and an electric field-forming means which forms an electric field in the reaction region by applying a potential difference in the reaction region, and the method includes at least a step of turning on/off the electric field formation by the electric field-forming means at a predetermined timing.

The electric field formed in the reaction region mainly carries out functions (1) to stretch the detecting substance and the target substance, such as nucleotide chains, (2) to move the target substance, which is separated from the detecting substance, back and forth along the electric lines of force, and (3) to adjust the higher-order structure of a reaction product (combination of the detecting substance and the target substance) obtained by the interaction between the detecting substance and the target substance to a structure in which it is possible to more accurately read fluorescence emitted from the fluorescently labelled target substance or a fluorescent intercalator that specifically binds to the reaction product.

That is, by forming a desired electric field (by applying a voltage) or not forming an electric field (removing a voltage) at a suitable, predetermined timing, functions (1) to (3) can be carried out in sequence.

More specifically, by applying a high frequency, high voltage, function (1) is carried out to prepare structures which allow the detecting substance and the target substance to easily react with each other, for example, linear structures (stretched structures) in which the base sequences of nucleotide chains are not folded.

Next, by applying a rectangular wave voltage (pulsed direct voltage), more specifically, by applying a rectangular wave voltage alternately (i.e., +/−), function (2) is carried out so that the target substance which is liberated in the reaction region is brought closer to the detecting substance which is immobilized on the detection surface. Consequently, since reaction efficiency (reaction opportunity) is increased, reaction time can be shortened.

In the detection stage, also by applying a high frequency, high voltage to the reaction region, function (3) is carried out so that the fluorescence or the like from the reaction product in the reaction region can be accurately detected by a detection means, such as an optical means.

In order to reliably carry out the interaction, such as a hybridization, between the detecting substance and the target substance, a reaction region is preferably prepared so that the interaction takes place mainly based on the Brownian movement of the substances. Therefore, in the present invention, in a series of electric field-forming steps, a period in which an electric field is not formed in the reaction region is positively provided. That is, subsequent to the period in which the rectangular wave voltage is on, by providing a period in which the rectangular wave voltage is off, the interaction between the substances can be accelerated.

Herein, in the "bioassay method" of the present invention, the types of detecting substance and target substance are not particularly limited. Examples of the "target substances" include substances labelled with fluorescent or other tags and substances not labelled. The "detecting substance" is not narrowly defined, and examples of detecting substances broadly include low-molecular substances, high-molecular substances, and biological substances which are solid-phased on the detection surface directly or indirectly through linkers and which specifically interact with the target substances labelled with fluorescent or other tags.

The "detection surface" means a surface site which is favorably surface-treated so that the ends of nucleotide chains or the like can be immobilized. For example, when surface treatment is performed with streptavidin, a detection surface suitable for immobilization of biotinylated nucleotide chains is obtained.

The method of the present invention is applicable to all of the interactions between high-molecular substances, such as protein-protein, nucleotide chain-nucleotide chain (including both DNA-DNA and DNA-RNA), protein-nucleotide chain (including double-stranded), and other interactions, interactions between a high-molecular substance and a low-molecular substance, and interactions between low-molecular substances.

For example, when the detecting substance and the target substance are nucleotide chains and the interaction is a hybridization, even in a small reaction region (spot region), the hybridization efficiency can be increased without fail. Consequently, it is possible to provide a novel DNA chip or microarray technique with a short reaction time and high accuracy in reading.

When the interaction between substances is a hybridization, the bioassay method preferably includes the steps of (a) forming an electric field so as to stretch the detecting nucleotide chain which is immobilized on the detection surface at the end, (b) adding the target nucleotide chain into the reaction region after step (a), (c) applying a potential difference in the reaction region to relatively move the detecting nucleotide chain and the target nucleotide chain in the reaction region after step (b), and (d) performing hybridization in a state in which a voltage is removed after step (c). Steps (a) to (d) will be specifically described below.

In the present invention, the term "nucleotide chain" means a polymer of a phosphoric ester of a nucleoside in which a purine or pyrimidine base is glycosidically linked to a sugar. Examples of nucleotide chains broadly include oligonucleotides, including DNA probes, polynucleotides, DNA (full length or its fragments) in which purine nucleotides and pyrimidine nucleotides are polymerized, cDNA (cDNA probe) obtained by reverse transcription, and RNA.

Since the detecting nucleotide chain (single-stranded) which is to be immobilized on the detection surface does not always have a linear conformation, the detecting nucleotide chain is linearly stretched along the electric lines of force by step (a). Thereby, the base sequence of the detecting nucleotide chain is exposed to the reaction region, and a state in which hydrogen bonding with a complementary base sequence easily occurs can be obtained.

More specifically, the nucleotide chain which comprises many polarization vectors composed of negative charges of the nucleotide chain having phosphate ions and positive charges of ionized hydrogen atoms is stretched by the application of an electric field, and thereby the bases are not superposed on each other any more. As a result, the steric hindrance disappears, and a hybridization reaction with the adjacent target nucleotide can be carried out smoothly.

The principle of stretch or movement of the nucleotide chain will be described in detail below. An ion cloud is thought to be produced by phosphate ions (negative charges) constituting the backbone of the nucleotide chain and hydrogen atoms (positive charges) formed by ionization of water in the vicinity thereof. The polarization vectors (dipoles) generated by the negative charges and positive charges are oriented in one direction overall by the application of a high frequency, high voltage, and as a result, the nucleotide chain is stretched. In addition, when a nonuniform electric field in which electric lines of force are concentrated in one region is applied, the nucleotide chain moves toward the region in which the electric lines of force are concentrated (refer to Seiichi Suzuki, Takeshi Yamanashi, Shin-ichi Tazawa, Osamu Kurosawa and Masao Washizu: "Quantitative analysis on electrostatic orientation of DNA in stationary AC electric field using fluorescence anisotropy", IEEE Transaction on Industrial Applications, Vol. 34, No. 1, p75-83 (1998)).

After step (a), step (b) is carried out in which a sample solution containing the target nucleotide chain is added into the liquid phase of the reaction region with the voltage being still applied or with the voltage being removed.

After step (b), step (c) is carried out in which an electric field is formed in the reaction region to relatively move the detecting nucleotide chain and the target nucleotide chain in the reaction region so that a reaction environment in which the hybridization easily proceeds is created. That is, according to step (c), by forming an electric field in the reaction region, the opportunity for reaction between the nucleotide chains, which has been mainly based on the Brownian movement, can be remarkably increased, and the reaction efficiency is increased, thus improving the detection accuracy.

Next, in step (d), after step (c), the voltage is removed, and a hybridization based on Brownian movement is performed. In step (d), the voltage is removed because the hybridization is a reaction which is mainly left to hydrogen bonding between complementary base pairs.

In another aspect of the present invention, a "bioassay apparatus" having the construction described below is provided as a tool for advantageously carrying out the bioassay method.

That is, the bioassay apparatus of the present invention includes a detecting element which includes at least a detection surface which is surface-treated for immobilizing a detecting substance, a reaction region which provides a field for interaction between the detecting substance immobilized on the detection surface and a target substance, and an electric field-forming means which can form an electric field in the reaction region by applying a potential difference and which can turn on/off the electric field formation at a predetermined timing.

The "detecting element" includes the detection surface, the reaction region, and the electric field-forming means as three essential components, and the other components and structures are not particularly limited. For example, a fine cell structure, channel structure, or the like, delimited from the periphery, may be formed on a substrate, and the essential components may be provided on the structure to form a detecting element. The number of detecting elements on the substrate may be determined depending on the purposes and applications, and any planar substrate, such as a rectangular or disc-shaped substrate, may be properly selected.

In another aspect of the present invention, a "bioassay substrate" having the construction described below is provided as a tool for advantageously carrying out the bioassay method.

The "bioassay substrate" of the present invention includes a "detecting element" provided on a disc-shaped substrate from which recorded information can be optically read, the detecting element including at least (1) a detection surface which is surface-treated for immobilizing the end of a detecting nucleotide chain, (2) positive and negative electrodes for forming an electric field to stretch the detecting nucleotide chain immobilized on the detection surface, and (3) a reaction region which provides a field for hybridization between the detecting nucleotide chain and a target nucleotide chain.

In the bioassay substrate having the "detecting element", an electric field is applied to the detecting nucleotide chain immobilized on the detection surface so that the nucleotide chain is linearly stretched, and then a sample solution containing the target nucleotide chain is accurately dripped onto the reaction region of the detecting element, and thereby the hybridization reaction between the detecting nucleotide chain and the target nucleotide chain is carried out. As a result, the hybridization reaction can be performed efficiently over a short period of time, which is advantageous.

Such an advantage is brought about by the following process. As described above, the nucleotide chain which comprises many polarization vectors composed of negative charges of the nucleotide chain having phosphate ions and positive charges of ionized hydrogen atoms is stretched by the application of an electric field, and thereby the bases are not superposed on each other any more. As a result, the steric hindrance disappears, and a hybridization reaction between the detecting nucleotide and the adjacent target nucleotide can be carried out smoothly.

The principle of stretch or movement of the nucleotide chain will again be described below. An ion cloud is thought to be produced by phosphate ions (negative charges) constituting the backbone of the nucleotide chain and hydrogen atoms (positive charges) formed by ionization of water in the vicinity thereof. The polarization vectors (dipoles) generated by the negative charges and positive charges are oriented in one direction overall by the application of a high frequency, high voltage, and as a result, the nucleotide chain is stretched. In addition, when a nonuniform electric field in which electric lines of force are concentrated in one region is applied, the nucleotide chain moves toward the region in which the electric lines of force are concentrated.

Herein, when an electric field is applied so that electric lines of force are concentrated on the detection surface, the nucleotide chain stretched by the electric field (described above) moves toward the detection surface, and the end portion impacts against the detection surface. Consequently, the detecting nucleotide chain can be reliably immobilized on the detection surface.

The "reaction region" is a delimited region or space which can provide a field for a hybridization reaction in the liquid phase, and which is a region where an electric field is formed in the liquid phase because of a potential difference generated between the positive and negative electrodes.

Furthermore, in the reaction region, in addition to the interaction between single-stranded nucleotides, i.e., hybridization, a desired double-stranded nucleotide may be formed from a detecting nucleotide chain, and then an interaction between the double-stranded nucleotide and a peptide (or protein) may be performed, or an oxygen response or other intermolecular interactions may be performed. For example, when the double-stranded nucleotide is used, it is possible to analyze the linkage between the receptor molecule, such as a hormone receptor, which is a transcription factor, and the responsive element DNA portion, etc.

In the bioassay substrate of the present invention, the "detecting element" may be a cell-type detecting element having a cell structure in which a detection surface is placed on one surface thereof, and a plurality of cell-type elements may be arrayed on a disc-shaped substrate. The "cell-type detecting element" is defined as a site having a cell-like reaction region which is delimited from the peripheral substrate region.

The "cell-type detecting elements" may be arrayed at appropriate positions on the substrate. By arraying the cell-type detecting elements radially when viewed from above, the space on the substrate can be effectively used, and thereby the integration density of information can be increased. That is, it is possible to provide a (disc-shaped) DNA chip with a large accumulation of recorded information.

Since the cell-type detecting elements are delimited from each other so as to prevent contamination, different detecting nucleotide chains may be immobilized for each cell-type detecting element or for each group of cell-type detecting elements so that hybridization reactions are carried out by setting different, independent conditions for the individual detecting nucleotide chains.

For example, marker genes used to identify the expression of a disease may be grouped and immobilized on a substrate. Thereby, it is possible to simultaneously identify the expression status of a plurality of diseases.

It is also possible to group the detecting nucleotide chains to be immobilized based on the difference in Tm or GC content. Consequently, the buffer composition, reaction conditions, such as the concentration, cleaning conditions, the concentration of a sample solution to be dripped, etc. to obtain an active hybridization reaction can be sensitively selected depending on the characteristics of the detecting nucleotide chain. Therefore, it is possible to significantly lower the risk that false positive or false negative results are shown in the analysis.

In the bioassay substrate of the present invention, a construction may be employed in which the reaction regions of the detecting elements are formed or arrayed in the grooves radially extending on the disc-shaped substrate and the detection surfaces are placed on the inner surfaces of the grooves.

The "groove" to be formed in the substrate means a long microchannel structure. One of the fields to which the bioassay substrate provided with the grooves belongs is a disc-shaped microchannel array. Hereinafter, the detecting element in which a reaction region is provided in the groove is referred to as a "groove-type detecting element", as in the "cell-type detecting element".

When the "groove-type detecting element" is employed, it is possible to feed a liquid using capillary action, or to use a liquid-feeding process in which the centrifugal force generated by rotating the disc-shaped substrate in a predetermined manner is utilized. For example, a sample solution, a cleaning liquid used for removing an excess target substance which is not actively linked after reaction, etc., can be fed smoothly and reliably from the central region of the substrate into the grooves (i.e., reaction regions).

In the groove-type detecting element, it is also possible to immobilize different detecting nucleotide chains for each groove or for each group of grooves.

In the bioassay substrate described above, when a means for providing the positional information of the detection surface site and rotational synchronization information is provided, it is possible to drip the detecting nucleotide-containing solution and the target nucleotide-containing solution into a predetermined reaction region by accurate tracking.

The means may be a wobbled groove or address pits provided on the substrate. "Wobbling" means to slightly meander the groove (pregroove) in which data is recorded by the user from side to side relative to the center of the track in order to preliminarily record information on physical addresses on the disc. Usually, FM modulation with a slight deviation of frequency is performed on a frequency higher than the tracking servo band, and the pregroove is formed on the substrate with a sinusoidal wave modulating signal amplitude as a radial deviation of the groove.

In the bioassay substrate described above, the reaction region may be filled with a material which can undergo a reversible phase change between gel and sol at between room temperature and the optimal temperature for the reaction (referred to as a "phase change material"). For example, an agarose gel may be used as the phase change material.

In such a case, it is possible to carry out a procedure in which the phase change material is solated under high temperatures; a voltage is applied in this state to array nucleotide chains, such as DNA; the phase change material is gelated by decreasing the temperature; and furthermore, the phase change material is solated under optimal temperature conditions for the reaction during hybridization. If the phase change material maintains the gelated state during hybridization, hybridization can be performed while the nucleotide chains, such as DNA, are stretched, which is preferable. Additionally, when the phase change material is gelated, there is a possibility that hybridization does not proceed successfully. Therefore, as in electrophoresis, a longitudinal recess may be preliminarily formed at the dripping point so that the sample solution is dripped into the recess.

In the present invention, the target nucleotide may be labelled with a fluorescent dye, or an intercalator may be used. The "intercalator" is incorporated into the hybridized double-stranded nucleotide chain in such a manner that the intercalator is inserted into the hydrogen bond between the bases of the detecting nucleotide chain and the target nucleotide chain. Thereby, the fluorescence wavelength is shifted toward the long-wavelength side, and also, since the fluorescence intensity and the amount of intercalator incorporated into the double-stranded nucleotide are correlated with each other, quantitative detection is enabled based on the correlation. As described above, the present invention has the technical advantage of providing a novel technique concerning DNA chips and biosensor chips.

The present invention also has the technical advantage of providing a novel bioassay substrate which can be used for analysis of gene mutations, SNP (single nucleotide polymorphism) analysis, gene expression frequency analysis, etc., to industries related to the development of new drugs, clinical diagnosis, pharmacogenomics, forensic medicine, and others.

BRIEF DESCRIPTION OF THE DRAWINGS

FIG. 6(A) is a top plan view of the substrate; and FIG. 6(B) is an enlarged plan view of the section X in FIG. 6(A).

BEST MODE FOR CARRYING OUT THE INVENTION

The preferred embodiments of the present invention will be described below based on the attached drawings.

FIGS. 1(A) to 1(F) are flowcharts which illustrate preferred steps of a bioassay method of the present invention and a preferred embodiment of a bioassay apparatus of the present invention. FIG. 2 is a waveform chart which illustrates an example of a step of applying/removing a voltage in the bioassay method or apparatus.

An example in which both the detecting substance and the target substance are single-stranded nucleotide chains and the interaction is a hybridization in the present invention will be described below. However, it is to be understood that the detecting substance and the target substance are not limited to nucleotide chains and that the interaction is not limited to a hybridization in the present invention.

Figure 1:
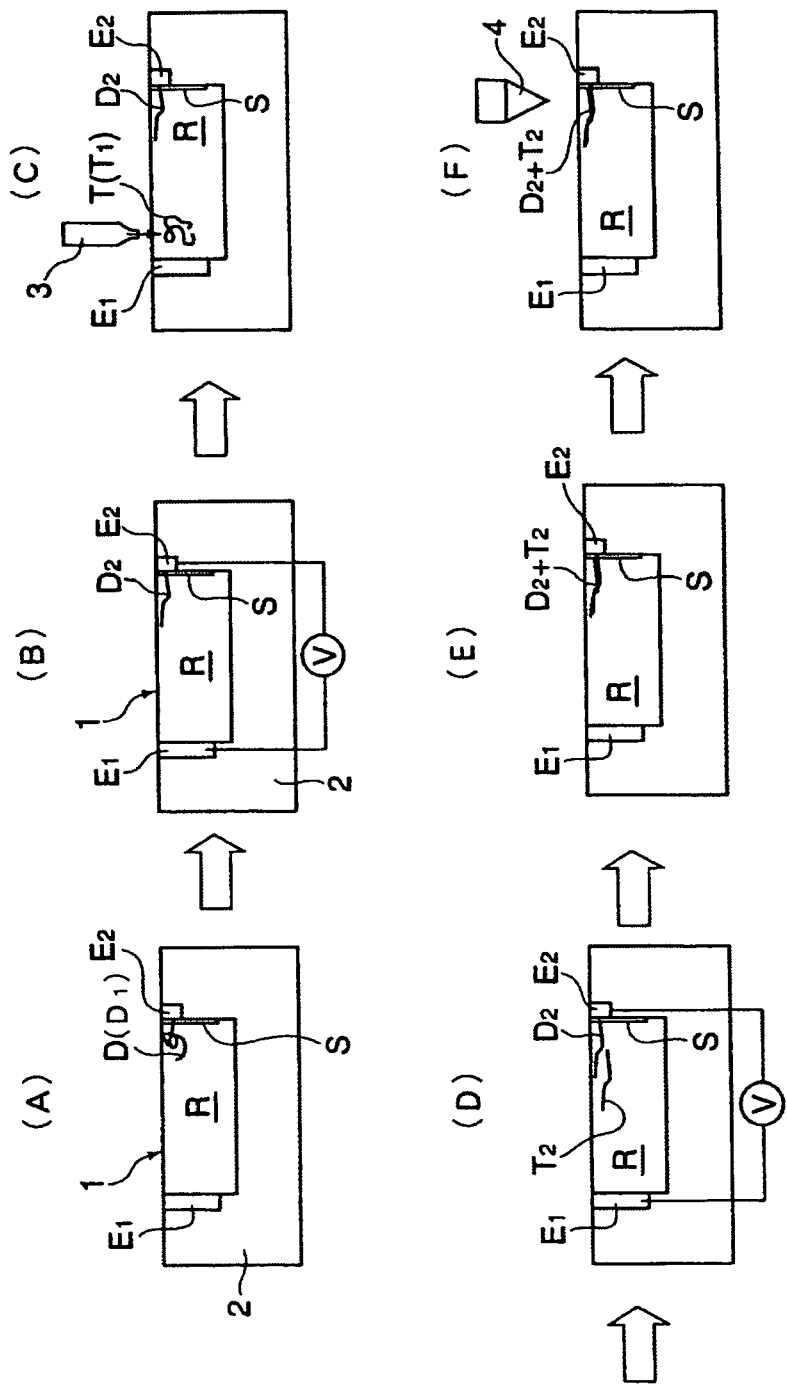
FIG. 1 is a flowchart which illustrates preferred steps of a bioassay method of the present invention and a referred embodiment of a bioassay apparatus of the present invention.
Figure 2:
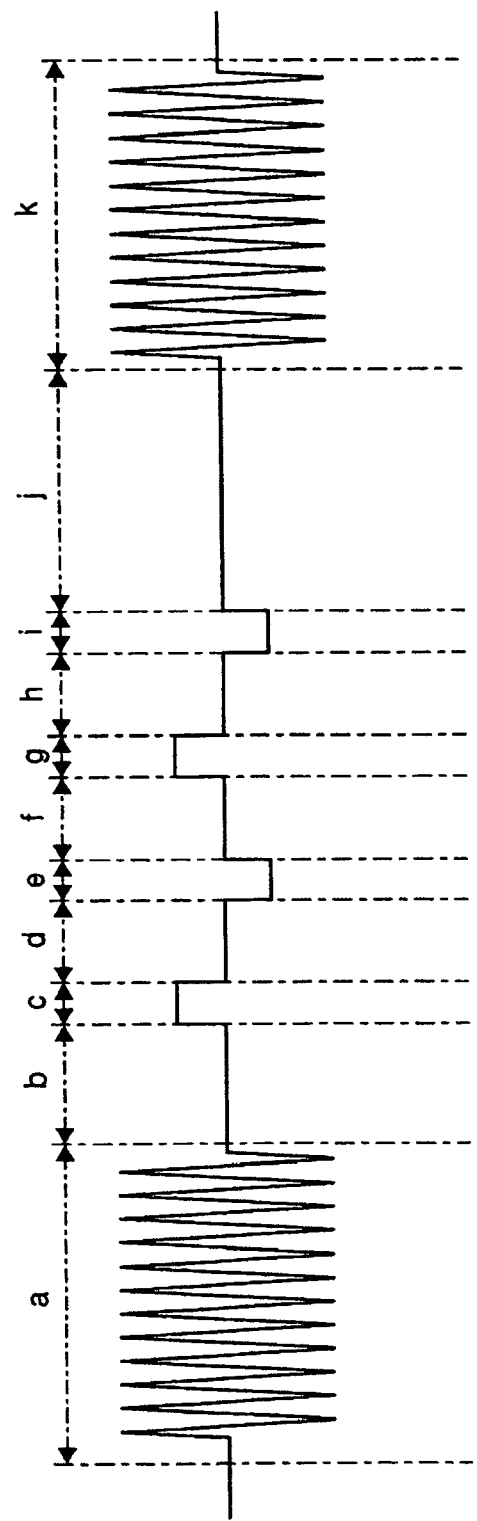
FIG. 2 is a waveform chart which illustrates an example of a step of applying/removing a voltage in the bioassay method or apparatus.

First, the bioassay method or bioassay apparatus of the present invention uses a detecting element 1 which includes at least a detection surface S which is surface-treated for immobilizing a detecting substance represented by symbol D in FIG. 1, a reaction region R which provides a field for interaction between the detecting substance D immobilized on the detection surface S and a target substance T, and a positive electrode E1 and a negative electrode E2 functioning as an electric field-forming means E which generates a potential difference in the reaction region R by applying a potential difference in the reaction region R. Reference numeral 2 represents a portion of a substrate provided with the detecting element 1, and symbol V represents a power supply for applying power to the positive electrode E1 and the negative electrode E2.

FIG. 1(A) briefly shows the state in which the end of a single-stranded detecting nucleotide chain (e.g., DNA probe) D1 is immobilized on the detection surface S. In this state, the higher-order structure of the detecting nucleotide chain D1 is not always linear, and is often, for example, as shown in FIG. 1(A), in a folded form as if the chain were tangled. Since all the base sequence is not always exposed to the reaction region R, it is considered to be difficult to efficiently perform a hybridization with the target nucleotide chain T which is later added into the reaction region R.

Therefore, in the present invention, a high frequency, high voltage is applied to the liquid phase (a salt solution or the like) in the reaction region R between the positive electrode E1 and the negative electrode E2 to generate a potential difference in the reaction region R, and thereby an electric field is formed. The electric field has a function to stretch the detecting nucleotide chain D1 linearly (straight) along the electric field. As a result, the detecting nucleotide chain D1 becomes stretched (represented by symbol D2), and the base sequence of the detecting nucleotide chain D1 is exposed to the liquid phase (refer to FIG. 1(B)).

Next, with the high frequency, high voltage being removed or being still applied, a sample solution containing the target substance T (target nucleotide chain T1) is added from a nozzle 3 with a predetermined structure accurately into the reaction region R. Although the target nucleotide chain T1 is not always linear at the time of addition, as shown in FIG. 1(C), in the liquid phase to which a high frequency, high voltage is applied, as shown in FIG. 1(D), the target nucleotide chain T1 becomes stretched linearly (represented by symbol T2). Thus, a state is created in which the stretched target nucleotide chain T2 and the similarly stretched detecting nucleotide chain D2 easily form a complementary strand.

Next, by repeating the step of applying/removing a rectangular wave voltage several times, the nucleotide chains D2 and T2 are brought close to each other stepwise, the target nucleotide chain is moved back and forth, or the reaction timing is adjusted.

The rectangular wave voltage is removed so that the complementary strand formation reaction, i.e., hybridization, between the linear target nucleotide chain T2 and the linear detecting nucleotide chain D2 is carried out mainly based on the Brownian movement. Furthermore, FIG. 1(E) briefly shows a double-stranded reaction product (D2+T2) formed by hydrogen bonding between the complementary base sequence portions of the chains D2 and T2.

In the present invention, in addition to the detection of the target nucleotide T1 (T2) having a base sequence that is complementary to that of the detecting nucleotide chain D1 (D2), further developments may be made, for example, a method in which, by using the steps described above, a desired double-stranded nucleotide chain (DNA) is prepared, and an interaction between a specific protein, such as a transcription factor, and the specific response sequence portion in the double-stranded nucleotide chain (DNA) is detected, and furthermore, search, assay, etc., of endocrine disrupters using the method.

FIG. 1(F) shows a step of detecting and reading the labelled (e.g., fluorescently labelled) target nucleotide chain T2 by an optical means 4. In the present invention, the labelling method is not narrowly limited. For example, a fluorescent intercalator may be used. The fluorescent intercalator is incorporated into the hybridized, double-stranded nucleotide chain so as to be inserted into the hydrogen bond between the bases of the detecting nucleotide chain D and the target nucleotide chain T. Thereby, the fluorescence wavelength is shifted toward the long-wavelength side, and also, based on the correlation between the fluorescence intensity and the amount of fluorescent intercalator incorporated into the double-stranded DNA, quantitative detection is enabled. As the fluorescent dye used for the fluorescent intercalator, POPO-1, TOTO-3, or the like may be selected.

In the detection stage, by applying a high frequency, high voltage, the higher-order structure of the reaction product (double-stranded nucleotide chain) formed in the reaction region R is adjusted to a structure that is not folded, and thereby, accurate detection can be performed by the optical means 4.

An example of a step of applying/removing a voltage will now be described with reference to FIG. 2. This example corresponds to the steps shown in FIG. 1(C) onward.

<Step a>

By placing a nucleotide chain in the electric field formed by the application of a high frequency, high voltage, induced polarization of the nucleotide chain is performed, and thereby the nucleotide chain is stretched. Consequently, in step a, by applying high frequency, high voltage, the target nucleotide chain T1 is stretched, and similarly the detecting nucleotide chain D1 is stretched (refer to the states shown in FIGS. 1(C) and 1(D)).

Additionally, the optimum conditions for the high frequency, high voltage, are considered to be $1 \times 10^6$ V/m, and about 1 MHz (refer to Masao Washizu and Osamu Kurosawa: "Electrostatic Manipulation of DNA in Microfabricated Structures", IEEE Transaction on Industrial Application Vol. 26, No. 26, p. 1165-1172(1990)).

<Step b>

At the timing in which the nucleotide chains D2 and T2 are believed to be relatively moved and brought close to each other, the voltage is removed, and hybridization is carried out mainly based on the Brownian movement (refer to the state shown in FIG. 1(E)).

<Step c>

By applying a rectangular wave voltage in the positive direction, the target nucleotide chain T2 which is still not close to the detecting nucleotide chain D2 is moved by the Coulomb force so that the target nucleotide chain T2 is located at the proper position for hybridization with the detecting nucleotide chain D2 (refer to the process from the state shown in FIG. 1(D) to the state shown in FIG. 1(E)).

<Step d>

The voltage is removed again, and the hybridization is carried out mainly based on the Brownian movement (refer to the state shown in FIG. 1(E)).

<Step e>

Next, by applying a rectangular wave voltage in the negative direction, the target nucleotide T2 which is still not close to the detecting nucleotide D2 is moved (refer to the process from the state shown in FIG. 1(D) to the state shown in FIG. 1(E)).

<Step f>

The voltage is removed again, and the hybridization is carried out mainly based on the Brownian movement (refer to the state shown in FIG. 1(E)).

<Step g>

By applying a rectangular wave voltage in the positive direction again, the target nucleotide chain T2 which is still not close to the detecting nucleotide chain D2 is moved (refer to the process from the state shown in FIG. 1(D) to the state shown in FIG. 1(E)).

<Step h>

The voltage is removed again, and the hybridization is carried out mainly based on the Brownian movement (refer to the state shown in FIG. 1(E)).

<Step i>

By applying a rectangular wave voltage in the negative direction again, the target nucleotide T2 which is still not close to the detecting nucleotide D2 is moved (refer to the process from the state shown in FIG. 1(D) to the state shown in FIG. 1(E)).

<Step j>

The voltage is removed again, and the hybridization is carried out mainly based on the Brownian movement (refer to the state shown in FIG. 1(E)).

<Step k>

The double-stranded nucleotide chain (D2+T2), which is the reaction product formed by the hybridization, is stretched under a high frequency, high voltage, and fluorescence reading is performed (refer to FIG. 1(F)).

With respect to the step of applying/removing the rectangular wave voltage, etc., an appropriate step or timing may be selected or determined depending on the type of the reaction product to be handled. The step or timing is not limited to the one described above. The frequency and the voltage may be appropriately determined depending on the purpose.

A bioassay substrate usable in the present invention and a bioassay apparatus associated with the substrate will now be described.

Figure 3:
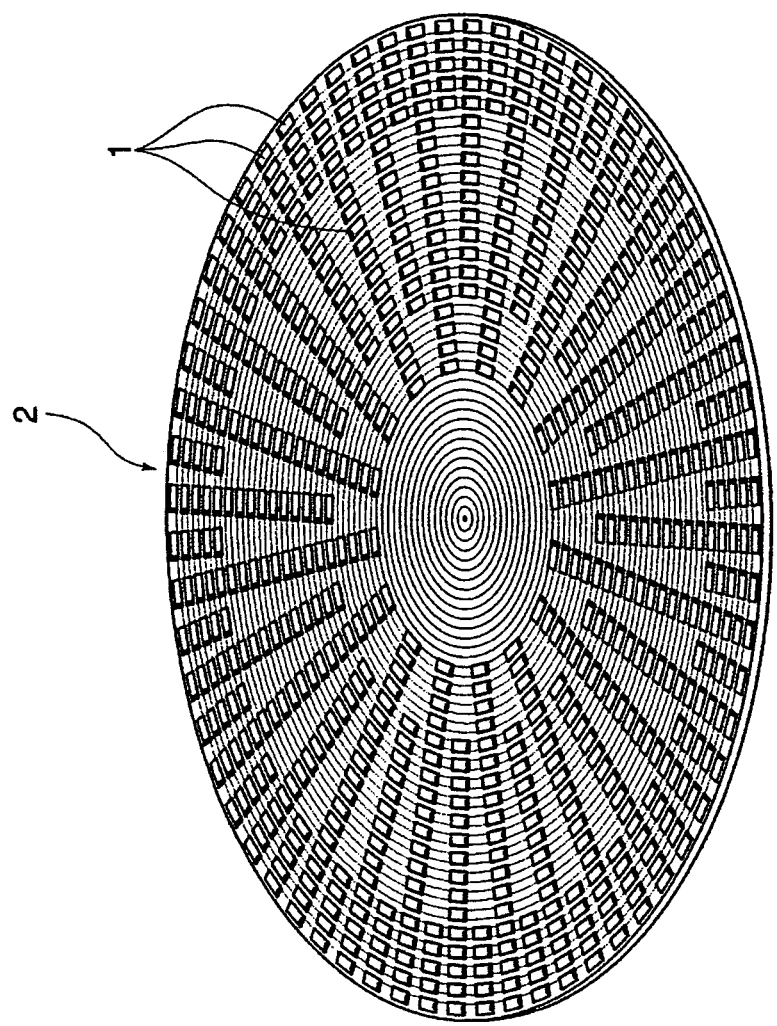
FIG. 3 is a perspective view showing the appearance of a bioassay substrate viewed from above in a preferred embodiment of the present invention.
Figure 4:
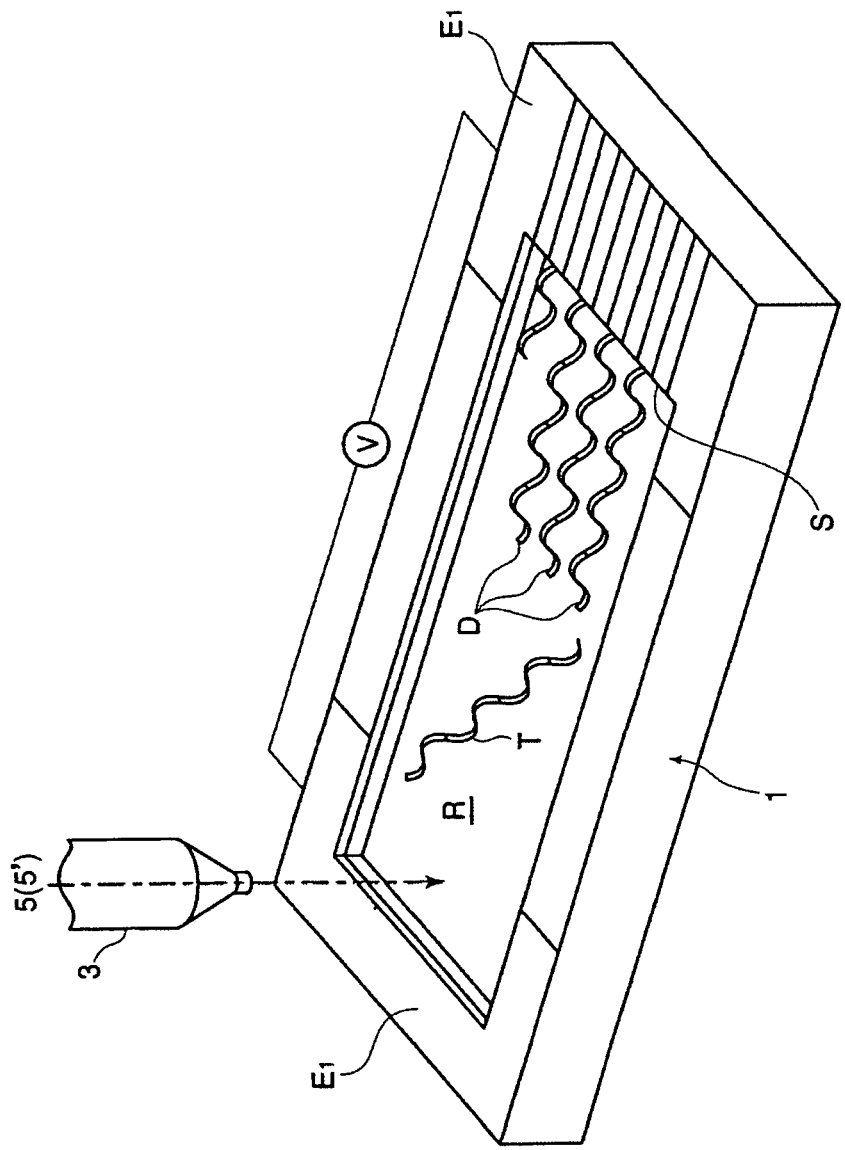
FIG. 4 is an enlarged perspective view showing a cell-type detecting element provided on a substrate.

FIG. 3 is a perspective view showing the appearance of a bioassay substrate provided with many detecting elements with a predetermined structure. FIG. 4 is an enlarged perspective view showing a "detecting element" provided on the substrate in a preferred embodiment. It is to be understood that the substrate usable in the present invention is not limited to the one shown in the drawing.

A bioassay substrate 2 shown in FIG. 3 includes a base plate for a disc-shaped substrate (disc) which is used for an optical information recording medium, such as CD, DVD, or MD. That is, in the substrate 2, recorded information can be read optically.

The base plate, which is composed of quartz glass, silicon, polycarbonate, polystyrene, or other synthetic resin which can be formed into a disc, and preferably injection-moldable synthetic resin, is formed into a disc. By using an inexpensive synthetic resin substrate, a low running cost can be achieved compared to the conventionally used glass chip. A hole (not shown in the drawing) for fixing a spindle which is used for rotating the substrate may be formed.

An evaporated aluminum layer is formed on one surface of the substrate 2 at a thickness of about 40 nm, and the layer functions as a reflecting film. In the reflecting film, the surface reflection is 4% or more from the base plate with a refractive index of 1.5 or more. A light-transmitting layer composed of a transparent glass, transparent resin, or the like is deposited on the reflecting layer.

Figure 6:
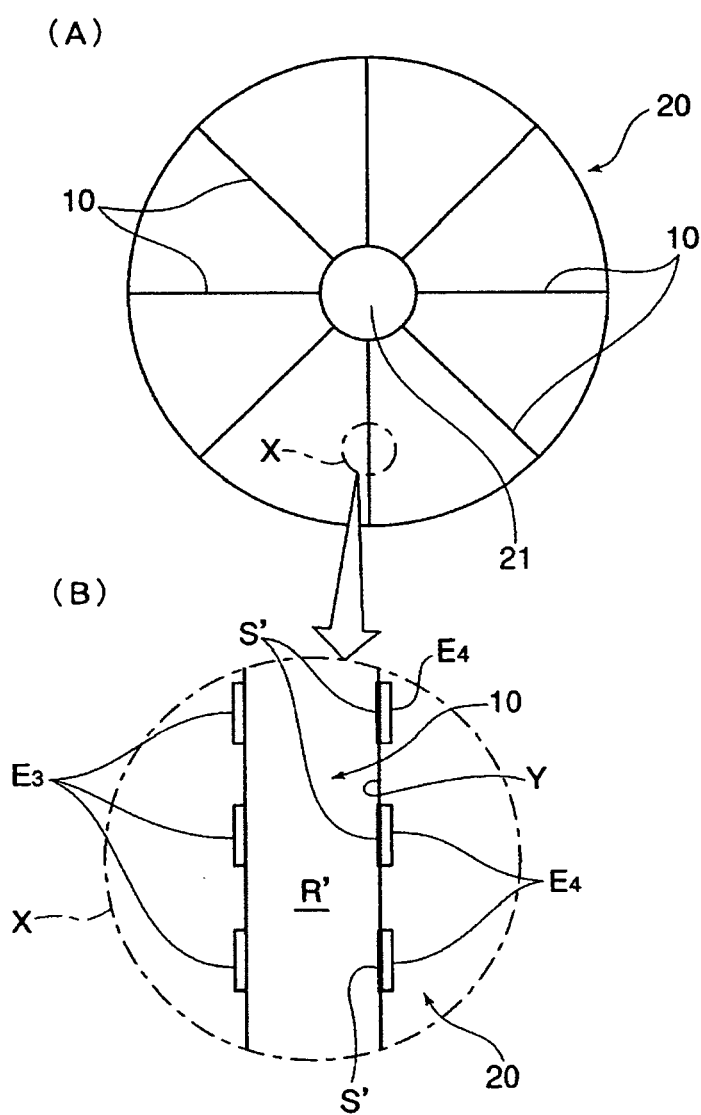
FIGS. 6(A) and 6(B) are diagrams showing a bioassay substrate in another preferred embodiment of the present invention.

Additionally, when the base plate is composed of a material with a high reflectance, it is not always necessary to form the reflecting film because the surface of the base plate itself functions as a reflecting surface. If a high-reflectance film, such as a metal film, is formed, the fluorescence intensity of a fluorescently labelled target substance can be detected with high sensitivity. The materials and the layer structure of the substrate 2 described above also apply to a substrate 20 which will be described below (refer to FIG. 6).

Many detecting elements 1 are arrayed on the light-transmitting layer so as to extend radially from the peripheral region of the center of the substrate 2 when viewed from above. FIG. 4 is an enlarged perspective view showing one of the cell-type detecting elements 1. With respect to the detecting elements 1, a case in which both the detecting substance and the target substance are single-stranded nucleotide chains will be described as a typical example. However, it is to be understood that the reaction substances detected by the detecting elements 1 are not limited thereto.

The reaction element 1 includes a detection surface S which is surface-treated for immobilizing the ends of detecting nucleotide chains represented by symbol D, a positive electrode E1 and a negative electrode E2 for forming an electric field to stretch the detecting nucleotide chains D preliminarily immobilized on the detection surface S, and a reaction region R which provides a field for hybridization between the detecting nucleotide chains D and target nucleotide chains T. In this example, the reaction region R is formed as a cell which opens toward the top and which is rectangular when viewed from above, for example, with a depth of 1 μm, a length of 100 μm, and a width of 50μ. However, the shape and size of the cell are not limited to those shown in the drawing.

The detection surface S is placed on the inner surface of the negative electrode E2 side facing the reaction region R. The detection surface S is suitably surface-treated so that the end of the detecting nucleotide chain D can be immobilized thereon by chemical bonding, such as coupling.

That is, the detection surface S is not particularly limited as long as it is surface-treated so that the preliminarily processed end of the detecting nucleotide chain D, such as a DNA probe, can be immobilized. For example, a detection surface S which is surface-treated which streptavidin is suitable for immobilization of the end of a biotinylated nucleotide chain.

A preferred method for immobilizing the detecting nucleotide chain on the detection surface S will be described below. By applying a nonuniform electric field to the reaction region R, the detecting nucleotide chain (which is liberated in the reaction region R) obtained by the action of the electric field moves toward the detection surface S in which the electric lines of force are concentrated, and the end portion of the detecting nucleotide chain impacts against the detection surface S. Consequently, the detecting nucleotide chain can be reliably immobilized on the detection surface S. In order to carry out this method favorably, the negative electrode E2 is shaped like a comb as shown in FIG. 4. Symbol V in FIG. 4 represents a power supply for applying power to the positive electrode E1 and the negative electrode E2.

In FIG. 4, reference numeral 4 represents a tip of a nozzle for dripping a sample solution 5. The nozzle 4 is constructed so that the sample solution 5 containing the detecting nucleotide chain D and a sample solution 5' containing the target nucleotide chain T are dripped into the position of the reaction region R by accurate tracking based on the positional information and rotational synchronization information provided by the substrate 2.

As the dripping means, an ink-jet printing method is preferably used. The reason for this is that a microdroplet can be accurately dripped into the predetermined reaction region R site (which also applies to a substrate 20 described below).

The "ink-jet printing method" is a method in which a nozzle used in an ink-jet printer is applied, and in which, using electricity, a detecting substance is ejected from a printer head and then is fixed, as in the ink-jet printer. Examples of the method include a piezoelectric ink-jet method, a bubble jet (registered trademark) method, and an ultrasonic jet method.

In the piezoelectric ink-jet method, a droplet is ejected by the pressure of displacement caused by the application of a pulse to a piezoelectric element. The bubble jet (registered trademark) method is a thermal method in which a droplet is ejected by the pressure of a bubble generated by activating a heater in a nozzle. A silicon substrate acting as a heater is embedded in the nozzle, and by controlling at about 300° C./s, uniform bubbles are formed, and droplets are ejected. However, since the liquid is exposed to high temperatures, care must be taken when this method is used for samples of biological substances. In the ultrasonic jet method, an ultrasonic beam is applied to the free face of a liquid so that a high pressure is applied locally, and thereby a droplet is ejected from that spot. A nozzle is not required, and a droplet with a diameter of about 1 μm can be formed at a high speed.

In the present invention, as the "ink-jet printing method", a "piezoelectric ink-jet method" is preferably used. Since the size of a droplet (microdroplet) can be controlled by changing the shape of the pulse to be applied, analysis accuracy can be improved advantageously. When the curvature radius of the surface of a droplet is small, the size of the droplet can be decreased. When the curvature radius of a droplet is large, the size of the droplet can be increased. By rapidly changing the pulse in the negative direction, the surface of a droplet is pulled inward so that the curvature radius is decreased.

Since many of the detecting nucleotide chains D dripped into the reaction region R are immobilized on the detection surface S with the bases being folded (refer to FIG. 1(A)), during hybridization with target nucleotide chains T which are dripped afterward, problems, such as steric hindrance, occur, and the reaction efficiency is low.

Therefore, based on the bioassay method of the present invention, power is applied to the positive and negative electrodes E1 and E2 to cause a potential difference in the reaction region R, and thereby an electric field is formed in the liquid phase (a salt solution) stored in the reaction region R so that the detecting nucleotide chain D and the target nucleotide chain are stretched linearly (straight) along the electric field.

Since steric hindrance, etc. is relieved, complementary base sequences easily come close to each other, and hydrogen bonding (complementary bonding) between bases of the linearly stretched detecting nucleotide chain D and the target nucleotide chain T which is labelled with a fluorescent dye or the like takes place efficiently.

That is, the hybridization reaction between the detecting nucleotide chain D and the target nucleotide chain T is carried out efficiently. Consequently, hybridization reaction time is shortened and the probability that false positive or false negative results are shown during reading is decreased, which is preferable.

Figure 5:
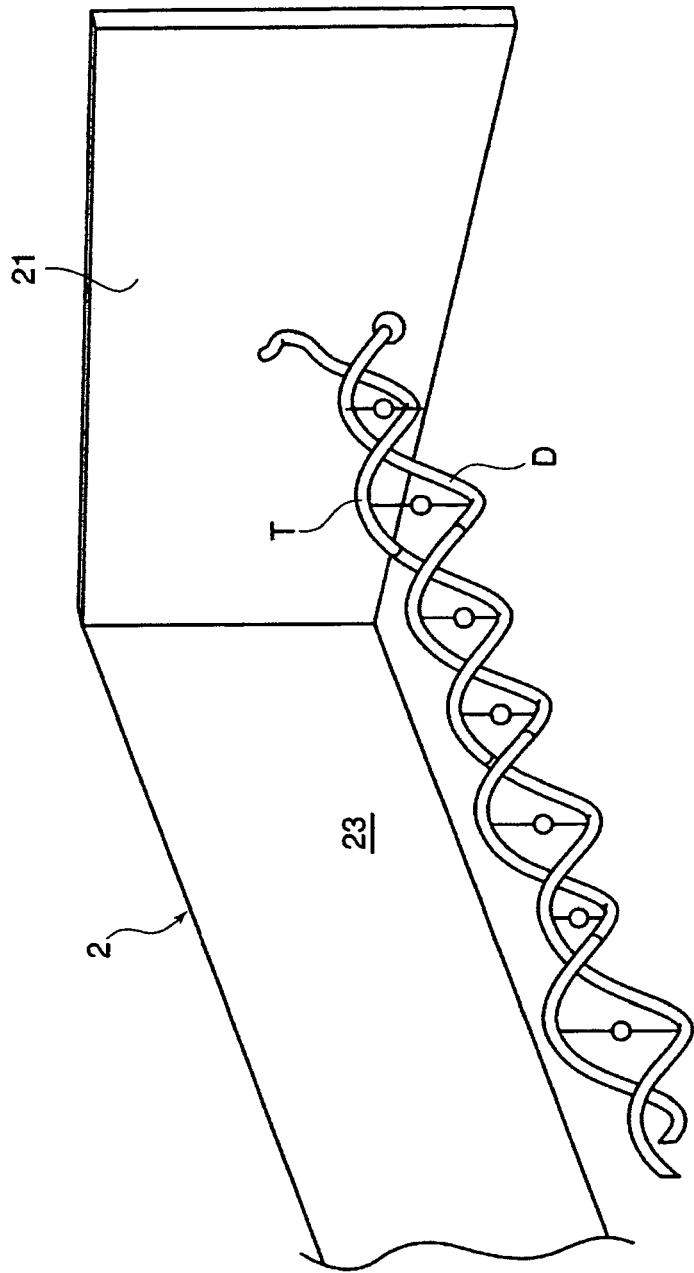
FIG. 5 is an enlarged view showing the detection surface and its vicinity of the reaction region of the cell-type detecting element.

FIG. 5 is an enlarged schematic diagram which shows the detection surface S and its vicinity of the reaction region R of the detecting element 1. FIG. 5 schematically shows a state in which a detecting nucleotide chain D of which end is immobilized on the detection surface S and a target nucleotide chain T having a base sequence that is complementary to the base sequence of the detecting nucleotide chain D are hybridized to form a double strand.

The reaction region R (or a reaction region R' which will be described below) may be filled with a phase change material, such as an agarose gel, which can undergo a reversible phase change between gel and sol (not shown in the drawing). In this embodiment, it is possible to carry out a procedure in which the phase change material is solated under high temperatures; a voltage is applied in this state to array nucleotide chains, such as DNA; the phase change material is gelated by decreasing the temperature; and furthermore, the phase change material is solated under optimal temperature conditions for the reaction during hybridization. If the phase change material is allowed to maintain the gelated state during hybridization, hybridization can be performed while the nucleotide chains, such as DNA, are stretched, which is preferable.

Additionally, when the phase change material is gelated, there is a possibility that hybridization does not proceed successfully when the sample solution 5' containing the target nucleotide chains T is dripped into the detecting element 1. Therefore, as in electrophoresis, a longitudinal recess may be preliminarily formed at the dripping point so that the sample solution is dripped into the recess.

The target nucleotide chain T may be labelled with a fluorescent dye, or an intercalator may be used. The intercalator is incorporated into the hybridized double-stranded nucleotide in such a manner that the intercalator is inserted into the hydrogen bond between the bases of the detecting nucleotide chain D and the target nucleotide chain T. Thereby, the fluorescence wavelength is shifted toward the long-wavelength side, and also, based on the correlation between the fluorescence intensity and the amount of intercalator incorporated into the double-stranded DNA, quantitative detection is enabled. As the fluorescent dye used for the intercalator, POPO-1, TOTO-3, or the like may be selected.

For example, it is possible to confirm the fact that a target nucleotide chain that is complementary to the detecting nucleotide chain D containing a marker gene which is known to be expressed when a particular disease occurs is resent in the sample solution 5' extracted from a given ell, or the like. As a result, the occurrence of the disease in the cell is predicted.

In order to read substrate information, the substrate 2 is irradiated with a laser beam (e.g., blue laser beam) to excite each reaction region R, the fluorescence intensity is detected by a detector (not shown in the drawing), and the state of bonding reaction between the detecting nucleotide chain D and the labelled target nucleotide chain is determined. Lastly, the fluorescence intensities for the individual reaction regions R are A/D converted and the distribution of bonding reaction rates is displayed on the screen of a computer C for visualization (which also applies to the substrate 20 described below).

A substrate in a second embodiment of the present invention will now be described with reference to FIGS. 6(A) and 6(B). FIG. 6(A) is a top plan view of a substrate 20 in the second embodiment, and FIG. 6(B) is an enlarged plan view of the section X in FIG. 6(A).

The substrate 20 shown in FIG. 6(A) and 6(B) is provided with groove-type detecting elements 10. The detecting elements 10 are formed as grooves in which reaction regions R' radially extend on a disc-shaped substrate. In each groove, detection surfaces S', each having the same structure as that of the detection surface S of the detecting element 1, are placed with a predetermined distance therebetween on the inner surface Y of one side in the longitudinal direction of the groove. At each site where the detection surface S' is formed, positive and negative electrodes E3 and E4 are provided so as to sandwich the reaction region R' (refer to FIG. 5(B)). Additionally, the groove-type detecting element 10 may be described as a structure in which the cell-type detecting elements 1 are arrayed in the groove.

The positive electrodes E3 may be formed as a common electrode, and similarly, the negative electrodes E4 may be formed as a common electrode. That is, the positive electrode E3 and the negative electrode E4, which are common electrodes, may be placed in parallel so as to face each other with the reaction region R' therebetween. In such a structure, current can be applied by pressing a needle probe to the positive electrode E3 and the negative electrode E4 from the above.

The reaction regions R' may be formed in pits (not shown in the drawing) which are arrayed in each groove. By dripping microdroplets into the reaction regions in the pits, it is possible achieve substantially the same spot size, and the fluorescence intensity can be detected with high reproducibility.

When the groove-type detecting element 10 is employed, it is possible to feed a liquid using capillary action, or to use a liquid-feeding process in which the centrifugal force generated by rotating the disc-shaped substrate in a predetermined manner is utilized.

Specifically, a liquid pool 21 is provided in the center of the substrate 20, and the sample solution 5 (5') (refer to FIG. 4), a cleaning liquid used for removing an excess target substance which is not actively linked after reaction, etc., is injected into the liquid pool 21. By rotating the substrate 20, the liquid can be smoothly and reliably fed from the central region of the substrate into the grooves (i.e., reaction regions R').

In each of the detecting element 1 of the substrate 2 and the groove-type detecting element 10 provided on the substrate 20, it is possible to immobilize different detecting substances D for each detecting element or for each group of detecting elements.

The positional information and the rotational synchronization information of the substrate 2 (20) will be briefly described below. Many address pits are preliminarily formed by an optical disc mastering process in the rotation direction of the substrate 2 (20). Assuming that the substrate 2 (20) is an optical disc, the reaction regions R (R') in which the liquid is dripped and detection is performed correspond to user data regions. In the other region, synchronous pits are arrayed by a sample servo method, or the like, and the other region is also used as a tracking servo. Furthermore, by inserting address parts (geographical addresses on the disc) immediately after the synchronous pits, positional information is provided.

The address part is a combination that begins with a sector mark which is a leading pattern, followed by a VFO (Variable Frequency Oscillator) which controls the rotational phase of the rotating disc, an address mark which shows the starting position of address data, and an ID (Identifier) including track and sector numbers.

In order to perform a bioassay using the substrate 2 (20), preferably, an apparatus including at least the following means and mechanisms is employed. That is, the apparatus (not shown in the drawing) includes at least a substrate rotating means which rotatably holds the substrate 2 (20); a dripping means which drips a detecting nucleotide chain-containing solution 5 and a target nucleotide chain-containing solution 5' into the reaction region R (R') at a predetermined sequence and timing while the substrate 2 (20) is being rotated by the substrate rotating means; a focus servo mechanism for maintaining a certain distance between (a nozzle of) the dripping means and the substrate 2 (20); and a tracking servomechanism which allows the solutions 5 and 5' to be dripped accurately into the reaction region R (R') of the substrate 2 (20) based on the positional information and rotational synchronization information provided from the substrate 2 (20).

Instead of using the address pits, addressing may be performed by a wobbled groove formed on the track, in which positional information on the disc is obtained by adjusting the wobble so as to have clock information according to the position. Simultaneously, by using the wobbling frequency, a tracking servomechanism is enabled. Furthermore, by forming both the address pits and the wobbled groove, addressing and tracking servo control can be performed more accurately.

By employing the substrate 2 or 20 and the bioassay apparatus including the substrate, the bioassay method of the present invention can be favorably performed.

In particular, in the bioassay substrate described above, the following advantages can be obtained.

That is, in the conventional DNA chip technology, since the integration degree and the integration density are low in the DNA chip itself, the amount of analysis that can be achieved in one assay is insufficient. Therefore, it is difficult for the user to freely set the types and numbers of detecting substances and furthermore the allocation (grouping) of the substances.

In the conventional DNA chip, since the nucleotide chain which is preliminarily immobilized on the surface of the substrate and which is used for detection is not necessarily held linearly, the accuracy in hybridization with the target nucleotide varies due to steric hindrance, etc., and a long period of time is required for the reaction.

Furthermore, in the conventional DNA chip in which DNA probes which are different in Tm (melting Temperature) or GC content, as detecting substances, are arrayed on the two-dimensional surface of the substrate, due to exposure to the same hybridization conditions and cleaning conditions, the risk that false positive or false negative results are shown is high.

In contrast, in accordance with the bioassay substrate of the present invention, the following great advantages can be obtained.

(1) In the bioassay substrate of the present invention, since large quantity and large number of detecting elements can be formed, a large accumulation of recorded information is enabled.

(2) An electric field is applied to a detecting nucleotide chain which is immobilized on the detection surface of the detecting element so that the nucleotide chain is linearly stretched, and then a sample solution containing a target nucleotide chain is accurately dripped into the reaction region of the detecting element. Thereby, hybridization is carried out between the detecting nucleotide chain and the target nucleotide chain. Consequently, hybridization can be performed efficiently over a short period of time.

(3) Since an assay can be performed by selecting optimal reaction conditions, etc., for each detecting element or for each group of detecting elements, the incidence of false positive or false negative results can be remarkably decreased. Consequently, in the bioassay substrate, it is possible to carry out analyses extensively, efficiently, and highly accurately, and moreover, the cost for recorded information is low.

(4) The bioassay substrate of the present invention is particularly useful as a DNA chip or biosensor chip. It is also possible to provide a disc-shaped microchannel array with a novel structure. The substrates of the present invention, as DNA chips, can be used for the analysis of gene mutations, SNP (single nucleotide polymorphism) analysis, gene expression frequency analysis, etc., and also can be used extensively for the development of new drugs, clinical diagnosis, pharmacogenomics, forensic medicine, and other fields.

Industrial Applicability

The present invention have the following specific advantageous effects.

(1) In the bioassay method or bioassay apparatus of the present invention, by controlling the timing of the electric field formation in a reaction region provided on the detecting element, the efficiency of the interaction between a detecting substance and a target substance in the reaction region can be improved, and it is possible to control the reaction timing.

(2) The present invention is particularly useful for bioassay methods based on DNA chips and biosensor chips, and can be used for the analysis of gene mutations, SNP (single nucleotide polymorphism) analysis, gene expression frequency analysis, etc., and also can be used extensively for the development of new drugs, clinical diagnosis, pharmacogenomics, forensic medicine, and other fields. Furthermore, the present invention can be used for the testing of antibody-antigen reactions, the assay of endocrine disrupters, etc.

The invention claimed is:

1. A bioassay apparatus comprising:
    a disk-shaped substrate having a groove radially extending on the disk-shaped substrate;
    a detecting element formed on the disk-shaped substrate, the detecting element comprising:
        positive electrodes formed on a first sidewall of the groove and negative electrodes formed on a second sidewall of the groove, the positive and negative electrodes being formed along a longitudinal direction of the groove and opposing each other;
        a detection surface formed on one of the positive and negative electrodes, the detection surface being treated to immobilize an end of a detecting substance on the detection surface;
        a reaction region sandwiched by the positive and negative electrodes for providing a field for interaction between the detecting substance immobilized on the detection surface and a target substance, wherein the reaction region contains a material which can undergo a reversible phase change between gel and sol at between room temperature and the optimal temperature for a reaction; and
        a power supply coupled with the positive and negative electrodes configured to form an alternating electric field in the reaction region before the interaction, so as to prepare the detecting substance to be reacted with the target substance;
    means for providing positional information and rotational synchronization information of the detecting elements;
    a dropping means configured to drip the target substance into the reaction region based on the positional information and rotational synchronization information; and
    a liquid pool provided in the center of the substrate configured to feed a cleaning liquid into the reaction region by rotating the substrate; wherein
    the power supply is further configured to apply a rectangular wave voltage in a positive direction or a negative direction to the reaction region for a first predetermined time period;
    the power supply is further configured to adjust the first predetermined time period according to a time required to relatively move the target substance to the detecting substance in the reaction region;
    the power supply is further configured to remove the rectangular wave voltage from the reaction region for a second predetermined time period; and
    the power supply is further configured to adjust the second predetermined time period according to a time required to perform the interaction between the detecting substance and the target substance.

2. A bioassay apparatus according to claim 1, wherein different detecting nucleotide chains are immobilized to each groove or a group of grooves.

3. A bioassay apparatus according to claim 1, wherein the means for providing positional information and rotational synchronization information of the detecting elements comprises a wobbled groove or address pits provided on the substrate.

4. A bioassay apparatus according to claim 1, wherein the detecting substance and the target substance are nucleotide chains and the interaction is hybridization.

5. A bioassay apparatus according to claim 4, wherein the hybridization is detected by an intercalator.

6. A bioassay apparatus according to claim 4, wherein the alternating electric field is stationary.

7. A bioassay apparatus according to claim 1, wherein the disk-shaped substrate is optically readable and includes a plurality of detecting elements.

8. A bioassay apparatus according to claim 7, wherein the detecting element is a reaction unit detecting element in which the detection surface is placed on one surface, and a plurality of reaction unit detecting elements are arrayed on the disc-shaped substrate.

9. A bioassay apparatus according to claim 8, wherein the reaction unit detecting elements are arrayed radially, when viewed from above, on the disc-shaped substrate.

10. A bioassay apparatus according to claim 9, wherein different detecting nucleotide chains are immobilized to each reaction unit detecting element or each group of reaction unit detecting elements.

11. A bioassay apparatus comprising:
    a disk-shaped substrate having a groove radially extending on the disk-shaped substrate;
    a detecting element formed on the disk-shaped substrate, the detecting element comprising:
        positive electrodes formed on a first sidewall of the groove and negative electrodes formed on a second sidewall of the groove, the positive and negative electrodes being formed along a longitudinal direction of the groove and opposing each other;
        a detection surface formed on a surface of one of the positive and negative electrodes and facing the other one of the positive and negative electrodes, the detection surface being treated to immobilize an end of a detecting substance on the detection surface; and
        a reaction region sandwiched by the positive and negative electrodes for providing a field for interaction between the detecting substance immobilized on the detection surface and a target substance, wherein the reaction region contains a material which can undergo a reversible phase change between gel and sol at between room temperature and the optimal temperature for a reaction;
    means for providing positional information and rotational synchronization information of the detecting elements;
    a dropping means configured to drip the target substance into the reaction region based on the positional information and rotational synchronization information;
    a liquid pool provided in the center of the substrate configured to feed a cleaning liquid into the reaction region by rotating the substrate; and
    means for controlling the interaction, further comprising:
        a power supply coupled with the positive and negative electrodes configured to form an alternating electric field in the reaction region before the interaction, so as to prepare the detecting substance to be reacted with the target substance;

the power supply is further configured to apply a rectangular wave voltage in a positive direction or a negative direction to the reaction region for a first predetermined time period;

the power supply is further configured to adjust the first predetermined time period according to a time required to relatively move the target substance to the detecting substance in the reaction region;

the power supply is further configured to remove the rectangular wave voltage from the reaction region for a second predetermined time period; and the power supply is further configured to adjust the second predetermined time period according to a time required to perform the interaction between the detecting substance and the target substance.

12. A bioassay apparatus according to claim 11, wherein the detecting substance and the target substance are nucleotide chains and the interaction is hybridization.

13. A bioassay apparatus according to claim 12, wherein the alternating electric field is stationary.

14. A bioassay apparatus according to claim 13, wherein the disk-shaped substrate is optically readable and includes a plurality of detecting elements.

* * * * *

UNITED STATES PATENT AND TRADEMARK OFFICE
CERTIFICATE OF CORRECTION

| | | |
|---|---|---|
| PATENT NO. | : 8,623,597 B2 | Page 1 of 1 |
| APPLICATION NO. | : 10/484134 | |
| DATED | : January 7, 2014 | |
| INVENTOR(S) | : Mamine et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 557 days.

Signed and Sealed this
Twenty-first Day of July, 2015

Michelle K. Lee
*Director of the United States Patent and Trademark Office*